United States Patent
Finch et al.

(10) Patent No.: US 6,482,197 B2
(45) Date of Patent: *Nov. 19, 2002

(54) METHODS AND APPARATUS FOR INHIBITING INFECTION OF SUBCUTANEOUSLY IMPLANTED DEVICES

(75) Inventors: Charles D. Finch, Clinton, MA (US); Jeffrey H. Burbank, Boxford, MA (US); James M. Brugger, Newburyport, MA (US); John H. Wang, North Andover, MA (US)

(73) Assignee: Vasca, Inc., Tewksbury, MS (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/932,455

(22) Filed: Aug. 16, 2001

(65) Prior Publication Data

US 2002/0055728 A1 May 9, 2002

Related U.S. Application Data

(63) Continuation of application No. 09/333,827, filed on Jun. 15, 1999, now Pat. No. 6,299,609, which is a continuation-in-part of application No. 09/161,044, filed on Sep. 25, 1998, which is a continuation-in-part of application No. 09/003,772, filed on Jan. 7, 1998, now Pat. No. 6,299,610.

(51) Int. Cl.$^7$ ............................................. A61M 31/00
(52) U.S. Cl. ....................................... 604/502; 604/506
(58) Field of Search ................................. 604/502, 506, 604/500, 175, 507, 508, 167.01, 167.02

(56) References Cited

U.S. PATENT DOCUMENTS

| | | | |
|---|---|---|---|
| 4,573,994 A | | 3/1986 | Fishell et al. |
| 4,579,554 A | | 4/1986 | Glassman |
| 4,767,411 A | | 8/1988 | Edmunds |
| 4,954,239 A | * | 9/1990 | Mueller ...................... 206/210 |
| 4,955,861 A | | 9/1990 | Enegren et al. |
| 4,959,054 A | | 9/1990 | Heimke et al. |
| 5,004,455 A | | 4/1991 | Greenwood et al. |
| 5,057,084 A | | 10/1991 | Ensmiger et al. |
| 5,185,003 A | | 2/1993 | Brethauer |
| 5,236,422 A | | 8/1993 | Eplett, Jr. |
| 5,261,896 A | | 11/1993 | Conway et al. |
| 5,263,930 A | | 11/1993 | Ensminger |
| 5,308,338 A | | 5/1994 | Helfrich |
| 5,482,740 A | | 1/1996 | Conway et al. |
| 5,529,189 A | * | 6/1996 | Feldschuh .................... 206/365 |
| 5,556,381 A | | 9/1996 | Ensminger et al. |
| 5,591,145 A | | 1/1997 | Sachse |
| 5,599,321 A | | 2/1997 | Conway et al. |
| 6,299,609 B1 | * | 10/2001 | Finch et al. ................. 604/502 |

OTHER PUBLICATIONS

Hemasite II® Product Brochure, Renal Systems,Inc. 14905 28$^{th}$ Avenue, North, Minneapolis, MN, 55441, USA, Telephone: 1–800–328–3340, 14 pages total.

* cited by examiner

Primary Examiner—Brian L. Casler
Assistant Examiner—Jeremy Thissell
(74) Attorney, Agent, or Firm—Townsend and Townsend and Crew LLP

(57) ABSTRACT

Implantable ports and other devices are cleansed by the injection of a washing solution into a region in the device or in a tissue pocket surrounding the device. In a first embodiment, the washing solution is injected through an aperture in the device to flush internal regions of the device before infusing the tissue pocket and flushing outwardly through a tissue tract leading to the device. In other embodiments, the washing solution is injected directly to a target site on the exterior of the device. Implantable devices may include special, usually hardened, target regions for receiving the sharpened end of a needle used to inject the washing solution. Kits will include devices, syringes, access devices, and instructions for cleansing according to the methods of the present invention.

12 Claims, 6 Drawing Sheets

METHODS AND APPARATUS FOR INHIBITING INFECTION OF SUBCUTANEOUSLY IMPLANTED DEVICES

CROSS-REFERENCES TO RELATED APPLICATIONS

This application is a continuation of application Ser. No. 09/333,827, filed Jun. 15, 1999 now U.S. Pat. No. 6,299,609, which is a continuation-in-part of application Ser. No. 09/161,044, filed on Sep. 25, 1998, which was a continuation-in-part of application Ser. No. 09/003,772, filed on Jan. 7, 1998 now U.S. Pat. No. 6,299,610, the full disclosures of which are incorporated herein by reference.

BACKGROUND OF THE INVENTION

1. Field of the Invention

The present invention relates generally to medical devices and methods. More particularly, the present invention relates to methods for inhibiting and treating the infection of implanted devices and to modified devices which facilitate such methods.

Subcutaneously and transcutaneously implanted devices are utilized for a wide variety of purposes. Heart pacemakers have become commonplace. Transvascular catheters are used for a variety of purposes, including hemodialysis access, drug infusion, and the like. Of particular interest to the present invention, subcutaneously and transcutaneously implanted ports and catheters have been proposed for both drug infusion and hemodialysis access. All such implanted devices are subject to infection. Subcutaneously implanted ports which are periodically accessed by needles and other percutaneously introduced devices are particularly subject to infections introduced by the access device.

Most infections of subcutaneously implanted ports begin as bacteria from the skin are carried into the tissue tract and port by the needle penetration. An infection can then grow internal to the port or within the tissue "pocket" which surrounds the port. A tissue pocket will form when the exterior surface of the port or other device is impermeable to tissue in-growth, e.g. where the surface is hard and composed of a metal, such as stainless steel, titanium, plastic, or the like. Infection can enter the space between the external surface of the device and the opposed tissue surface and can spread throughout the tissue pocket and sometimes into adjacent spaces, e.g. the space around a cannula attached to the port and leading to a blood vessel or other body lumen. While initially localized, the infection can become systemic and place the patient at significant risk.

Heretofore, infections of subcutaneously implanted devices have usually been treated by the systemic administration of antibiotics to the patient after infection has become established. Often, the implanted device must also be removed and replaced, subjecting the patient to additional trauma and leaving the patient without benefit of the device for the time it takes to clear the infection and replace the device. Moreover, the need to administer antibiotics periodically to patients is expensive and patients who suffer from repeated infections often become resistant to particular antibiotics.

As an alternative to antibiotic treatment and/or device removal, U.S. Pat. No. 5,263,930 proposes to provide a disinfectant reservoir in an implantable vascular access port. The reservoir includes a septum to permit periodic replenishment with a suitable anti-microbial agent. Agent introduced into the reservoir flows into an access lumen through the device. Catheters and other devices inserted into the access lumen become coated with the anti-microbial agent to provide a barrier against infection along the percutaneous access route. In particular, the design is intended to prevent infection of the bloodstream. While potentially beneficial, the provision of a static volume of antimicrobial agent within a reservoir does not provide flushing and active decontamination of the tissue pocket surrounding the implanted port. Thus, should bacteria be introduced into the tissue pocket, it is unlikely that the anti-microbial agent would be effective to inhibit infection.

In addition to the procedural shortcomings described above, conventional treatments with antibiotics and other anti-microbial agents are undesirable because of the nature of the antibiotic and anti-microbial agents themselves. Many patients are allergic to antibiotics and other anti-microbial agents. Additionally, the repeated use of antibiotics to treat recurrent infections (of the type which would often be associated with implanted devices) can often lead to antibiotic resistance which, over time, can render further antibiotic treatments ineffective.

For these reasons, it would be desirable to provide improved methods and devices for inhibiting bacterial and other infections in subcutaneously implanted devices. It would be particularly desirable to provide methods and devices for active flushing of the implanted device as well as the tissue pockets and regions surrounding the device in order to maximize the disinfection process. It would be particularly useful if such methods and devices could use washing solutions which are free from antibiotics and/or other biologically active agents intended for killing the bacteria associated with an infection. It would be still further desirable if such methods and devices were applicable not only to implantable ports but also to other subcutaneously and transcutaneously implanted devices. At least some of these objectives will be met by the present invention as described hereinafter.

2. Description of the Background Art

U.S. Pat. No. 5,263,930 has been described above. A transcutaneous vascular access port sold under the tradename HEMASITE® II by Renal Systems, Inc., Minneapolis, Minn., includes an above-skin reservoir for a bactericide, as described in a brochure entitled Vascular Access System copyrighted by the manufacturer in 1984. Catheters having bactericidal coatings and release capabilities are described in U.S. Pat. Nos. 5,599,321; 5,591,145; 5,482,740; 5,261,896; 5,236,422; 5,004,455; 4,959,054; 4,767,411; and 4,579,554.

SUMMARY OF THE INVENTION

The present invention provides methods and improved apparatus systems, and kits for inhibiting and/or treating infection of subcutaneously and transcutaneously implanted devices. As used hereinafter, the phrase "inhibiting infection" will refer to both prophylactic treatment to avoid infection and therapeutic treatment to eliminate an established infection. The methods and apparatus are particularly applicable to treatment of implanted vascular and other access ports which are at substantial risk of infection through repeated percutaneous access via needles, access cannulas, stylets, and the like. The present invention, however, will also be useful with a variety of other subcutaneously implanted devices, including pacemakers, catheters, prosthetic joints, defibrillators, implantable infusion pumps, and the like.

The present invention relies on percutaneous injection of a washing solution in an amount sufficient to flush a region within and/or surrounding the device. For prophylactic treatment, the washing solution may be any one of a variety of conventional washing solutions used for irrigation, lavage, and the like. Suitable washing solutions include saline, normal saline, and the like. While these solutions may include buffers, preservatives, and other conventional additives for washing solutions, they will generally be free from antibiotics and anti-microbial agents at a level which would have a microbicidal effect when administered to subcutaneous device sites according to the methods of the present invention.

For treatment of established infection, the washing solution will usually be the same, although in some cases the treatment may be supplemented with the systemic administration of an antibiotic, such as penicillin, vancomycin, and the like. Suitable anti-microbial agents for treating established infection are taught in copending application Ser. Nos. 09/161,044 and 09/003,772, the full disclosure of which have previously been incorporated herein by reference. The washing solution will be flowable so that it can be percutaneously introduced to the implanted device, usually being in the form of a liquid, although it could also be a flowable gel, and will usually be injected at a volume in the range from about 0.5 ml to 1000 ml, often from 1.0 ml to 500 ml, more often from 2.0 ml to 100 ml, and typically from 5.0 ml to 50 ml. Injection will conveniently be effected using a needle which can be penetrated directly through the skin, typically in combination with a conventional syringe.

The ability of the present invention to inhibit infection, either prophylactically or in the case of established infections, depends on the ability to flush the subcutaneously implanted device as well as the surrounding tissue, tissue pocket, and other sites where bacteria may accumulate and proliferate. Thus, it will generally be preferred to introduce volumes of the washing solution which are in substantial excess over the available void volume in the device in the surrounding tissue pocket. For most devices, it will be desirable to introduce a volume of the washing solution which is at least twice that of the combined void volume and internal volume of the tissue pocket, preferably being at least three times such volumes, more preferably being at least five times such volumes, and sometimes being at least ten times such volumes, or greater. Thus, the volume of washing solution introduced will depend to a great extent on the size of the implanted device and tissue pocket surrounding the device. Usually, volumes of washing solution as set forth above will be sufficient.

The extent and nature of the region which is flushed will depend greatly on the geometry and type of the implanted device. For implanted devices having internal spaces, such as implanted ports having apertures for receiving percutaneous access tubes, it will usually be desirable to flush at least the internal space with the washing solution. Preferably, at least a portion of any tissue pocket surrounding the implanted device will also be flushed with the washing solution. More preferably, a sufficient amount of the washing solution will be introduced to flush outwardly through the access tissue tract which is used to introduce the flushing needle and/or to subsequently introduce an access tube. In particular, the present invention is able to cleanse the tissue tract used for subsequently introducing an access tube.

For transcutaneously implanted device, i.e. devices which pass through an access site in the patient's skin (such as transcutaneous catheters), the washing solution is preferably introduced at a site just proximal to an infection barrier, such as an infection-inhibiting cuff on the catheter. In this way, the washing solution can be flushed outwardly back through the tissue track surrounding the catheter or other device and through the access site in the skin. The ability to flush the bacteria from the tissue region surrounding the transcutaneous catheter or other transcutaneous device is particularly beneficial in inhibiting infection.

In a preferred aspect of the method of the present invention, the subcutaneously implanted device is a port which is connected to a blood vessel, other body lumen or cavity, or solid tissue target site, usually using a cannula. The port has an aperture for receiving a percutaneous access tube, e.g. a needle. The washing solution is injected directly into the aperture to flush both the aperture and any internal volume surrounding or in fluid communication with the aperture, with excess washing solution being flushed from the aperture to infuse a region or space surrounding the port within the tissue pocket in which the port has been implanted. After flushing the access cannula will be introduced to the implanted port and a fluid transferred between the access cannula and the port as described previously in application Ser. No. 08/857,386, now U.S. Pat. No. 5,931,801. Exemplary fluids are blood and drug solutions. Usually, the port will be valved or have a septum to isolate the access aperture from that portion of the port which is connected to the cannula and/or the blood vessel or body lumen. Thus, flushing of the port with the washing solution can be performed without introduction of the solution beyond the valve, i.e. into the blood vessel or other target site. The needle used to flush the access port will be introduced in a manner which does not open the valve structure or septum, thus maintaining isolation. The needle used to introduced the washing solution, however, will usually be introduced through the same site or tissue tract as the primary access tube, thus reducing patient trauma. The washing needle will usually be smaller than the access tube, even further reducing patient trauma.

The methods of the present invention are also useful for flushing and inhibiting infection with ports and other subcutaneously implanted devices which do not have open access apertures. In such cases, it will usually be unnecessary to flush internal portions of the device, and the washing needle can be contacted directly against an external surface of the device in order to infuse the washing solution within the tissue pocket surrounding the device. Optionally, the needle may be contacted against a specially configured target site on the device, e.g. a well or other region on the device composed of or lined with a relatively hard material that can withstand repeated contact with the washing needle. The well or other target can be located by the treating professional, e.g. by manually feeling it through the skin, and will be positioned to permit the washing solution to flush freely about the exterior of the device at the interface between the device and the tissue. In some cases, it may be desirable to connect the well to channels or other surface features which permit the washing solution to suffuse freely around the periphery of the device.

In yet another embodiment, the methods may be used to wash transcutaneously implanted devices, such as catheters. In such cases, the washing solution is infused into the tissue pocket formed about the device, usually by injection into tissue through a location adjacent to device penetration site. As with previous embodiments, the washing solution is able to suffuse and flush the tissue pocket, and the excess washing solution will flow outward around the device onto the patient's skin, to assure thorough cleansing.

In an alternative aspect, a method according to the present invention for detecting infection of an implanted device comprises injecting a washing solution through a tissue tract into a region within or surrounding at least a portion of the device. The washing solution will usually be saline, water, or other sterile material which can flow into the region, flush the region, and carry visible products of infection back outwardly through the tissue tract. At least a portion of the injected material will flow outwardly back through the tissue tract in order to transport visible material resulting from infection back to the surface of the skin. By then observing that portion of the injected material which flows outwardly from the tissue tract, a determination can be whether an infection exists. Usually, the material which is initially injected will be relatively clear. If the material which is flushed from the tissue tract is milky and contains considerable debris, it is likely that an infection has become established. In that case, the infection may be treated by irrigating the device with a large volume of a washing solution according to the present invention. Alternatively or additionally, the patient could be treated with systemic antibiotics or in other conventional ways.

The present invention still further provides systems for cleansing and accessing an implanted port. The systems will comprise a needle adapted to deliver a washing solution to the implanted port, typically according to the methods described above. Usually, the needle will be attached to a syringe, and the syringe will usually be pre-filled with a suitable washing solution. The types and amounts of washing solution will be generally as described above. The system will still further include an access tube suitable for percutaneously coupling to the implanted port to deliver or receive a flowable material therefrom, e.g. in the case of ports connected to the vasculature. In other instances, the washing solution may be dialysate used in peritoneal dialysis. The access tube may also be in the form of a needle, and will usually be connected to a catheter having a hub or other structure at its proximal end for connecting to external equipment. Such systems may further comprise instructions for delivering the washing solution to the implanted device through the needle and thereafter for connecting the access tube to the implanted port after it has been cleansed. Optionally, the systems may be packaged together in conventional packages, such as pouches, trays, tubes, boxes or the like.

The present invention still further comprises kits including one or more of the apparatus and system components described above together with instructions for use according to any of the methods described above. For example, a kit according to the present invention may comprise any implantable device, such as an implantable port intended for percutaneous access via an access tube as described above, together with instructions for use for inhibiting infection of the device by introducing a washing solution to the device after it has been implanted. A second exemplary kit might comprise a container holding a volume of the washing solution, e.g. a syringe holding the washing solution having a needle for introducing the solution through the percutaneous tissue tract. The container or syringe would be combined in a kit with instructions for use setting forth methods for introducing the washing solution from the container through a tissue tract or injection site to an implanted device. A third exemplary kit would include the container and instructions for use, as just described, further in combination with an access tube intended for accessing an implantable port. A fourth exemplary kit would include the access tube together with instructions for use for introducing a washing solution through a tissue tract prior to introducing the access tube through the same tissue tract. All of the above kits will typically be placed together in a common package, such as a pouch, box, tube, tray, or the like. More usually, all kit components will be sterilized within the packaging and will be available for immediate use after the package is opened.

DESCRIPTION OF THE SPECIFIC EMBODIMENTS

Figure 1A:
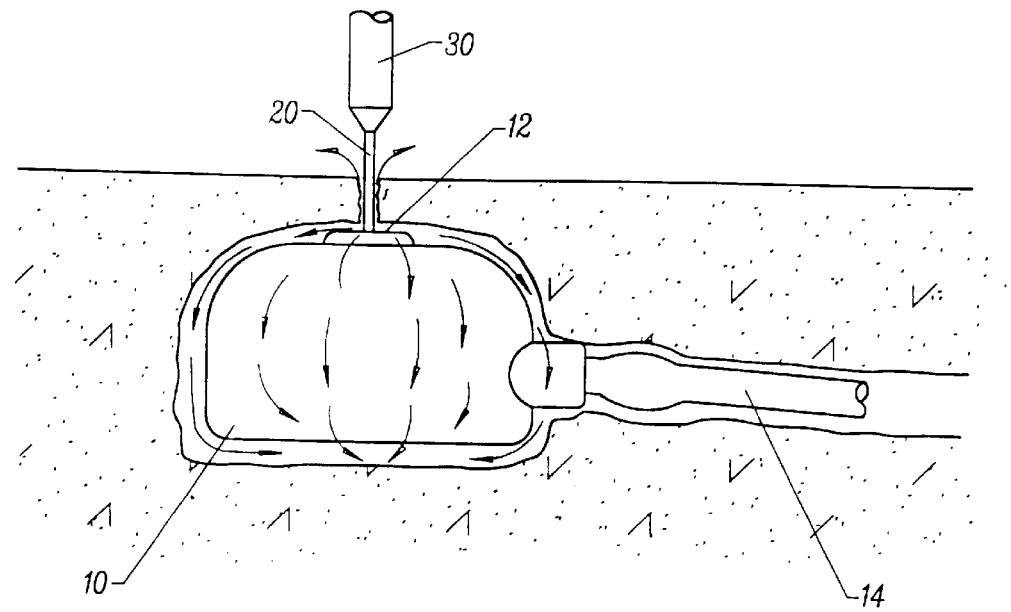
FIG. 1A illustrates an implanted vascular port having an access aperture being cleansed according to the method of the present invention.

The present invention provides novel methods for cleansing subcutaneously and transcutaneously implanted devices subject to such infection. The methods rely on injecting a suitable washing solution into a region or regions within a subcutaneous pocket into which the device has been previously implanted. Optionally, the washing solution will be injected through an aperture in order to flush internal spaces within the device, where excess washing solution will then suffuse outwardly through the same aperture and infuse into the tissue pocket. Alternatively, the washing solution may be injected directly onto a target site on the exterior of the device. In both cases, it will be greatly preferred to introduce a sufficient volume of the washing solution so that the solution will flush the tissue pocket as well as any open internal spaces within the device, and the spent washing solution will then flow outwardly through the tissue tract to carry bacteria and other contaminating substances away from the implantation site. Thus, it will be preferred to introduce the washing solution in large excess volume so that the tissue pocket and any open volume of the device will be substantially completely flushed and most or all of the contaminating materials be carried away. Flushing need only reduce the bacterial load sufficiently to enable the patient's immune system to suppress the remaining bacteria.

The washing solution is usually in a liquid form, e.g., such as saline, sterile water, Ringer's solution, or the like.

Alternatively, the washing solution may be in the form of a gel, emulsion, suspension, paste, powder, or other injectable fluid or material of a type normally employed in pharmaceutical uses.

The washing solution will be injected in an amount sufficient to flush at least a portion of the region surrounding the subcutaneously or transcutaneously implanted device, referred to herein as the "tissue pocket." Usually, the volume of washing solution injected will be sufficient to flush through the entire tissue pockets surrounding device preferably at least several times. When injected only on the exterior, the volume will usually be at the lower end of the ranges set forth above, e.g. from 0.5 ml to 10 ml. Often, however, in cases where internal portions of the device are also being flushed, the volume will usually be greater, i.e. being sufficient to completely fill and flush the internal regions as well as having sufficient excess to infuse through at least a portion, and preferably all, of the tissue pocket. Preferably, the volume will be sufficient to further express outwardly from the tissue pocket through the needle puncture site to flush potentially infecting organisms away from the implanted device and tissue tract. Such volumes will be in the range from 0.5 ml to 50 ml. In the case of implanted access ports, the volume will typically be in the range from 0.5 ml to 25 ml, more usually from 1 ml to 10 ml.

When cleansing an implanted port having a predefined tissue tract leading to the port, as generally described in co-pending application Ser. Nos. 08/896,592 and 08/071,241, it will usually be desirable to flush the tissue tract as well as the device and tissue pocket or other space surrounding the device prior to and/or after the device being accessed. As the pre-existing tissue tract will be used to subsequently introduce an access device, e.g. a large bore needle, it will be desirable to leave a portion of the washing solution within the tissue tract to cleanse the site and carry away bacteria that may be present on the access device as it is introduced. As will be described in more detail hereinafter. Introduction of the washing solution using a needle placed through the preexisting tissue tract will normally result in a portion of the washing solution being flushed out through the tissue tract to provide the desired cleansing.

Figure 2:
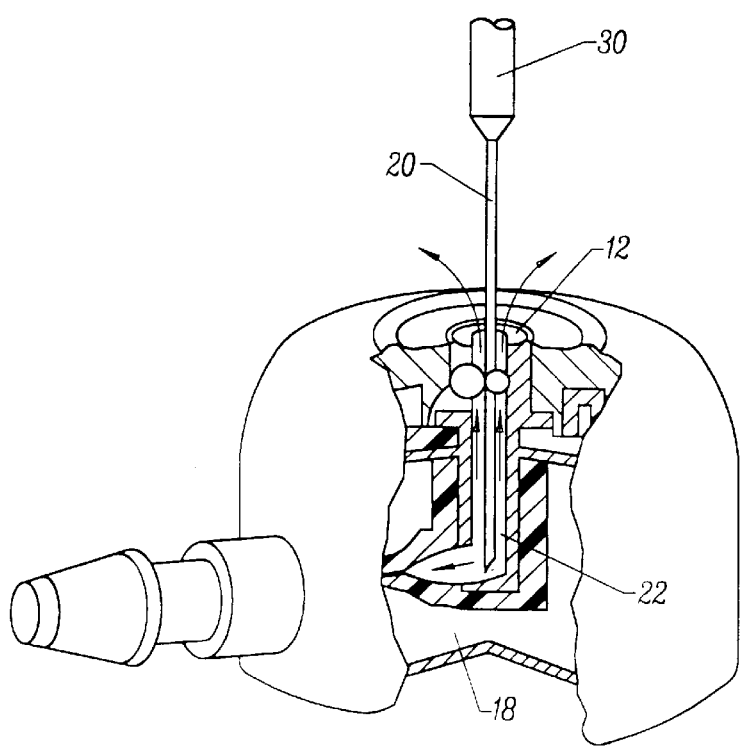
FIG. 2 is a detailed view of the port of FIG. 1, with portions broken away, illustrating the flow of washing solution within the internal regions of the port.
Figure 1B:
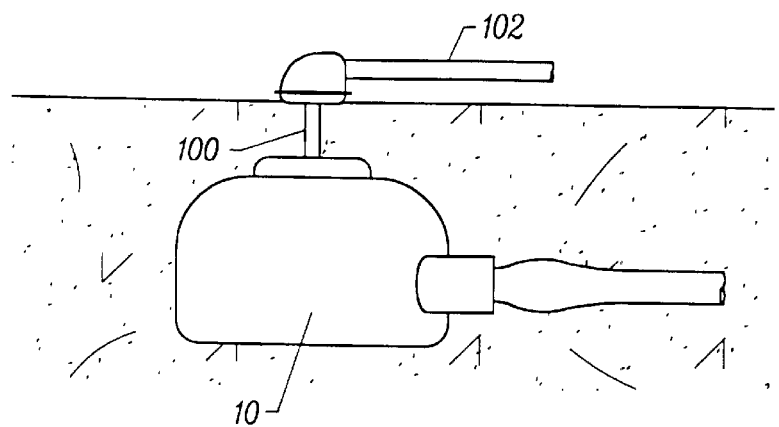
FIG. 1B illustrates the implanted vascular port of FIG. 1A having an access tube introduced through the tissue tract after the device, tissue pocket, and access tissue tract have been cleansed.

Referring to FIGS. 1A, 1B and 2, a first exemplary method according to the present invention will be described. A subcutaneously implanted port 10 is of the type which includes an aperture 12 for receiving a percutaneously introduced access tube (not shown), of the type described in co-pending application Ser. No. 08/857,386, filed on May 15, 1997, assigned to the assignee of the present invention, the full disclosure of which is incorporated herein by reference. In normal use, the access tube is introduced through the aperture 12 and a fluid is transferred between the access tube and an implanted cannula 14, which may be connected to a blood vessel, the peritoneal cavity, or other target site within the patient. The port 10 further comprises a valve structure 18, where the valve is normally closed, i.e. closed in the absence of the access tube. For the purposes of the present invention, the details of the valve mechanism 18 are unimportant. It is important only that the valve is actuated when a relatively large access tube is introduced through the aperture 12, e.g. a fourteen gauge access tube in the case of the specific port 10 described in the co-pending application.

Cleansing of the port 10 is accomplished using a needle 20 which is smaller than the access tube which is normally used to access the port. For example, a twenty-five gauge needle 20 may be introduced through the aperture 12 and substantially to the bottom of a vertical access path 22, as best seen in FIG. 2. The needle encounters a metal surface at the bottom of the access path 22, so the valve structure 18 is not damaged. Introduction of the smaller needle 20 does not actuate the valve mechanism, so the valve 18 remains closed, isolating the aperture 12 and access path 22 from the cannula 14.

After the needle 20 is in place, as shown in FIGS. 1A and 2, the washing solution may be injected using a syringe assembly 30 connected to the needle 20, in a conventional manner. Valve ports 10 of the type described in the co-pending application, a volume of washing solution in the range from 3 ml to 10 ml has been found to be sufficient to both irrigate and flush the access path 22 and associated interior volumes of the port as well as flush about the exterior of the port, as shown by the arrows in FIG. 1A. The injection of washing solution may be performed before access with an access tube, after access with an access tube, or at any other time. A particular advantage of the method illustrated in FIGS. 1A and 2 lies in the fact that no additional tissue access tract needs to be formed in order to introduce the washing solution. That is, the needle 20 may be introduced through the normal tissue tract which is formed in order to access the port with the access tube.

After the needle 20 is removed from the tissue tract, an access tube 100 may be introduced through the tissue tract to the port 10, as illustrated in FIG. 1B. The access tube 100 will typically be connected to a catheter 102 which may be connected to any external device or source needed for performing a procedure, e.g. a hemodialysis machine, a dialysate source for performing peritoneal dialysis, or the like.

Figure 3:
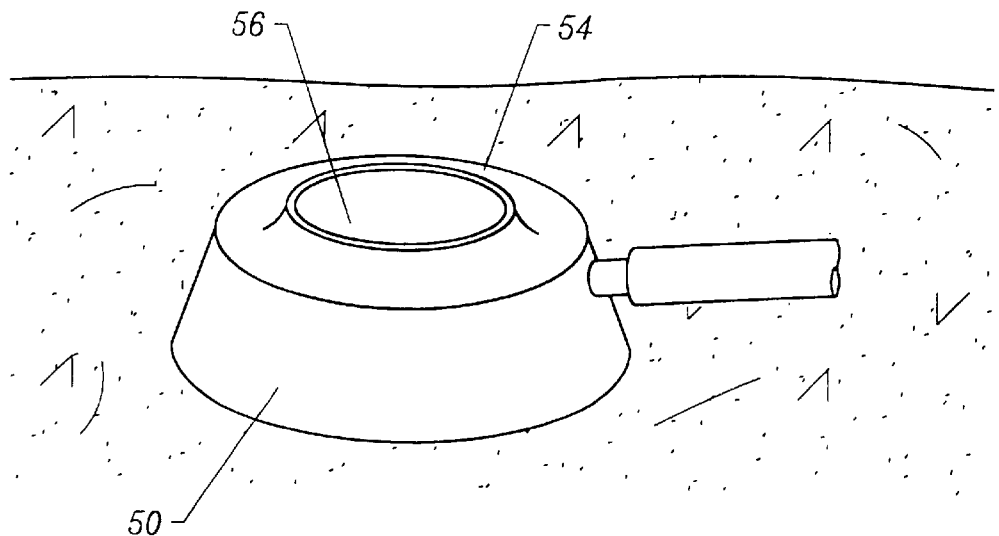
FIG. 3 illustrates an implanted port which has been modified to facilitate cleansing according to the methods of the present invention.
Figure 4:
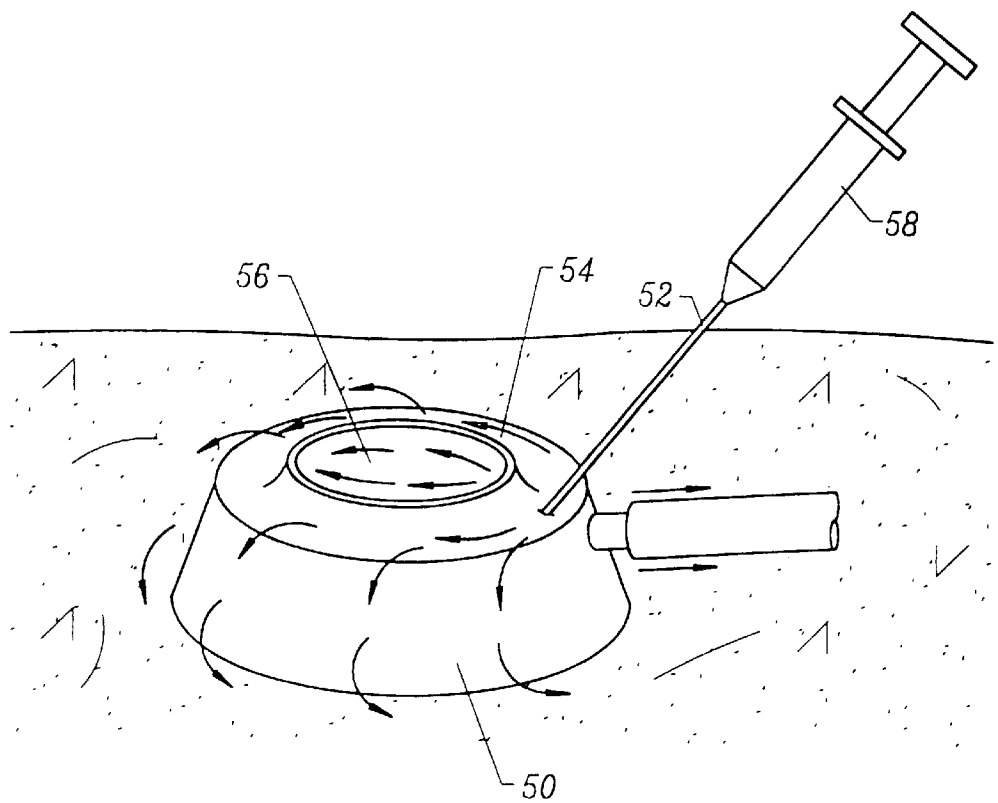
FIG. 4 illustrates a port of FIG. 3 undergoing such cleansing.

The cleansing methods of the present invention are also useful with a wide variety of other implanted devices. For example, as illustrated in FIGS. 3 and 4, a septum-type port 50 may be washed by engaging a needle 52 against an exterior surface of the device, and injecting a suitable washing solution using a syringe 54. Optionally, the port 50 may be modified to have a target site or region 54, which is shown to be in the form of an annular trough formed concentrically about the septum 56. It will be appreciated that many implantable devices have smooth surface which are difficult to contact with a needle and/or silicone rubber or other penetrable surfaces which will be penetrated by any needle used to introduce a washing solution. By providing a non-penetrable target site, usually being formed of a material which is harder than the needle to be used, engagement of a needle against the device can be facilitated. Trough structures, such as trough 54, also serve to distribute the washing solution about at least a portion of the exterior of the device to facilitate and enhance infusion of the washing solution over all portions of the surrounding tissue pocket.

Figure 5:
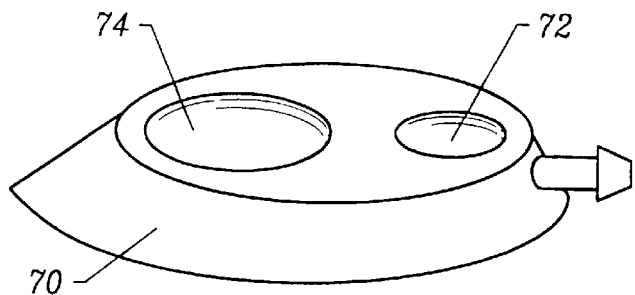
FIG. 5 illustrates an alternative embodiment of an implantable port which has been modified according to the present invention.

An alternative septum-type port 70 having a circular needle target site 72 is illustrated in FIG. 5. In that embodiment, the target is a simple conical indentation in the metallic body of the port 70. The target site 72 is laterally spaced-apart from the septum 74. The treating professional can manually locate a target site 72 and percutaneously access the target site using a needle to introduce the washing solution in a straightforward manner.

Figure 6:
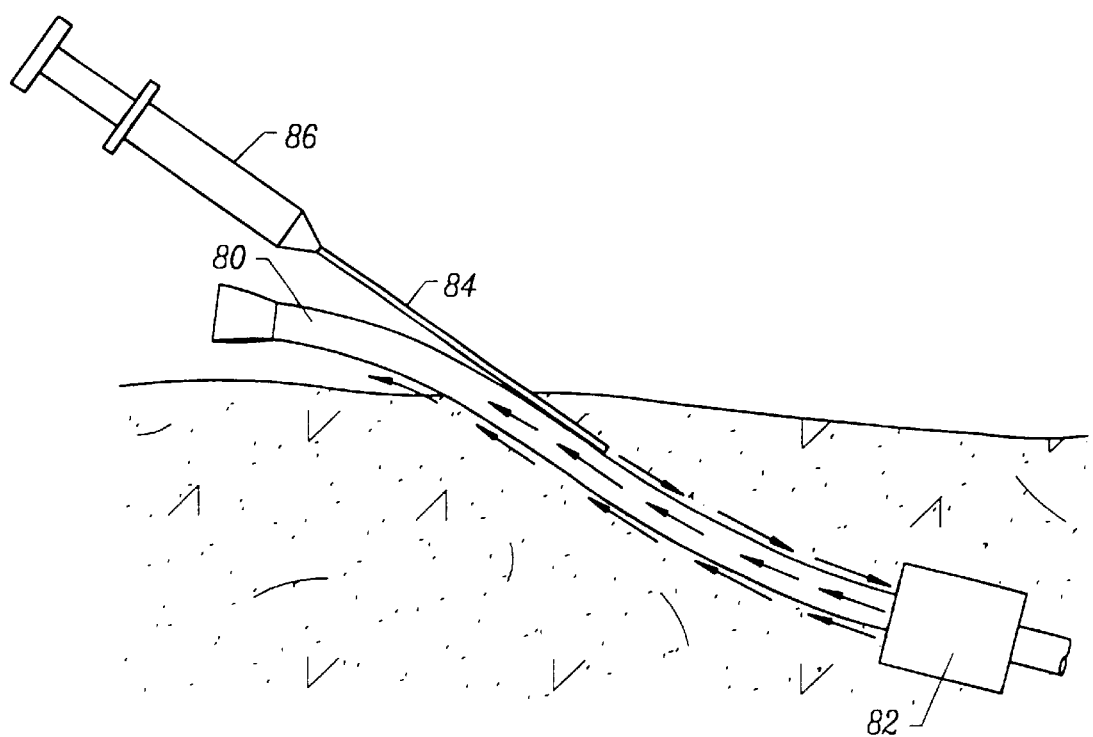
FIG. 6 illustrates a transcutaneously implanted catheter undergoing cleansing according to the method of the present invention.

The methods of the present invention are also suitable for cleansing transcutaneously implanted devices, such as transcutaneous catheter 80, as illustrated in FIG. 6. Transcutaneous catheters are provided for a variety of purposes, including hemodialysis and peritoneal dialysis access. A free, proximal end of the catheters generally remains accessible above a patient's skin, while a cuff 82 acts as an infection barrier below the skin. While the cuff 82 is generally effective to prevent the progress of an infection down the catheter, there is still a region between the cuff and the skin surface which is subject to infection. The present invention can be used to flush that area with a washing solution using a needle 84 and syringe 86, as shown in FIG. 6. The needle 84 is introduced through the percutaneous tissue opening, and the needle tip inserted along the tunnel/tract surrounding the catheter. The syringe 86 is then used to inject the washing solution into the tissue pocket until it encounters the implanted cuff 82. Preferably, the needle 84 will be blunt at its tip in order to avoid damage to the catheter. Alternatively, the catheter could be clad with a protective sheath for use with a sharp needle. The washing solution will thus generally fill and flush the tissue pocket and eventually pass outwardly through the region surrounding the transcutaneous penetration on the patient's skin surface.

Figure 7:
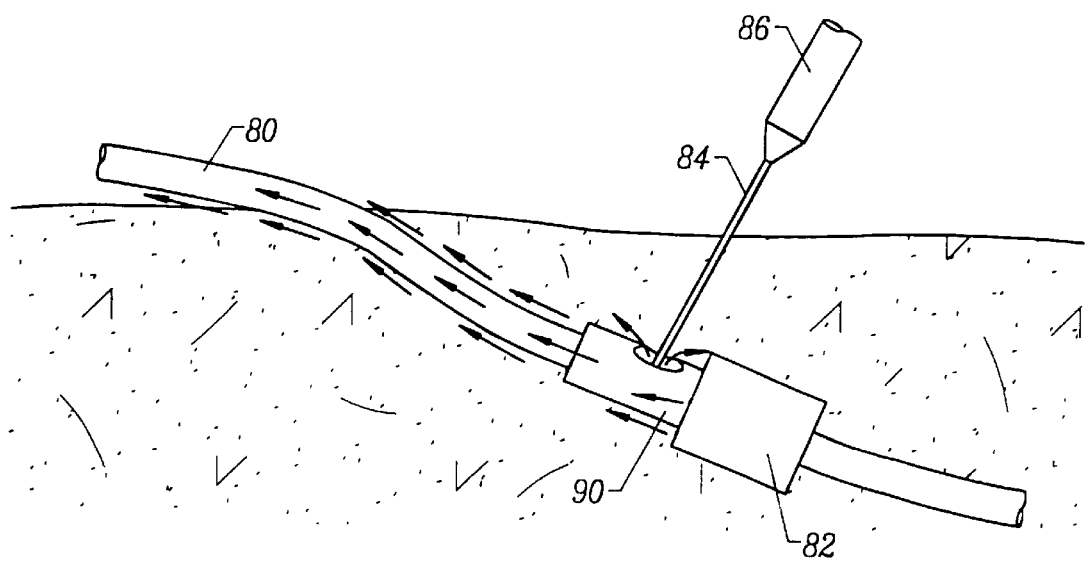
FIG. 7 illustrates a transcutaneously implanted catheter which has been modified to facilitate cleansing according to the methods of the present invention.

Transcutaneous catheters of the type illustrated in FIG. 6 may be improved by providing a hardened target region 90, preferably at a location immediately proximal of the implantable cuff 82, as shown in FIG. 7. The target region may be in the form of a metal sleeve having a conical or other depression designed for receiving the sharpened distal end of needle 84. The needle 84 may then be percutaneously introduced through the skin so that its distal tip engages the target region 90. The washing solution may then be injected from the region immediately adjacent the implanted cuff 82 so that the washing solution flows generally outwardly, as illustrated by the arrows of FIG. 7. Such one-way flushing may in some instances provide a more effective cleansing action.

Figure 8:
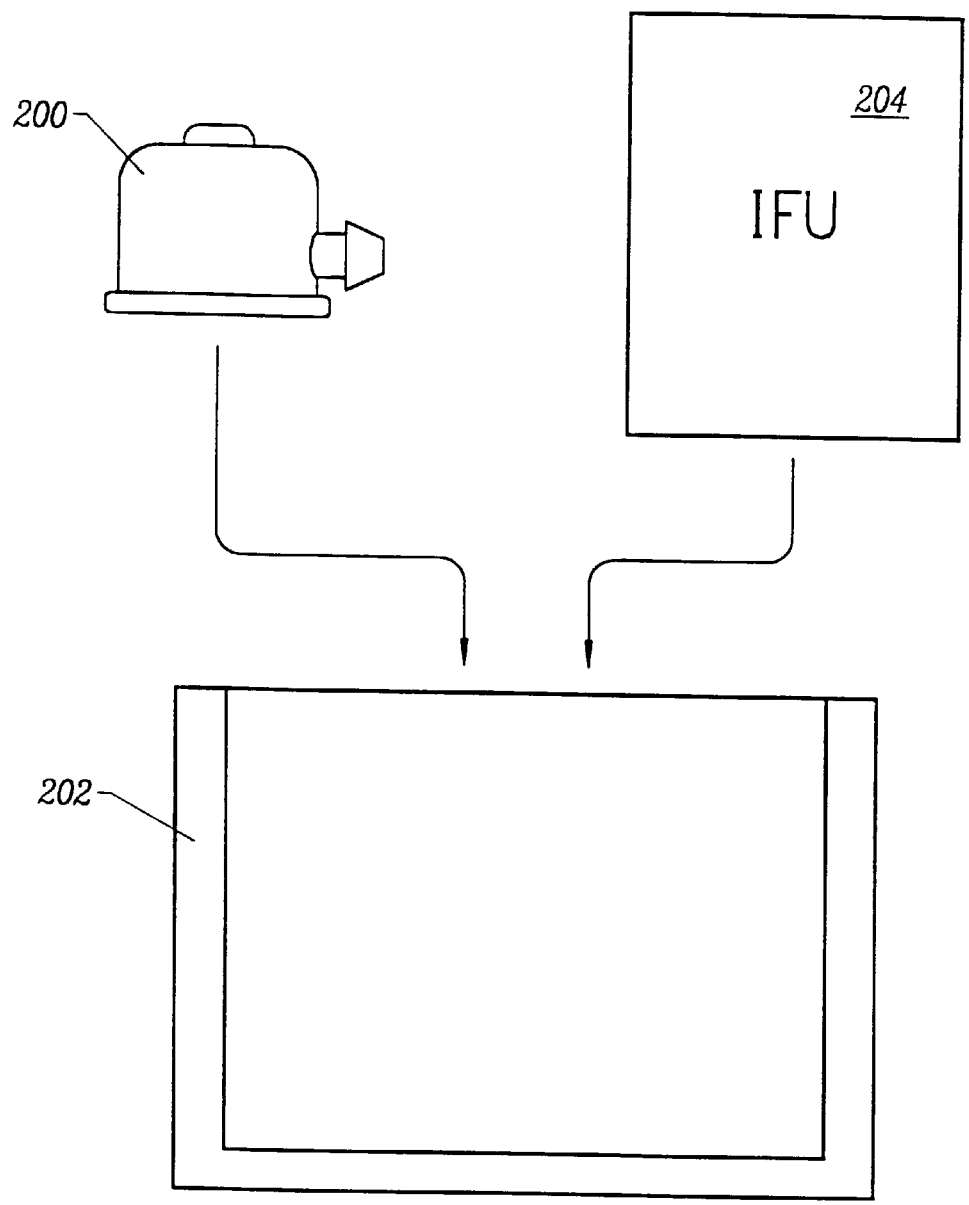
FIG. 8 illustrates a kit according to the present invention comprising an implantable port, instructions for use, and a package.

Referring now to FIG. 8, an implantable device 200, illustrated as an implantable port, may be packaged together with instructions for use (IFU) in a kit. The implantable device will typically be packaged in a pouch, tube, tray, box, or the like, or any other type of container 202. The IFU's may be printed on a separate sheet of paper 204 and/or may be printed on the packaging material itself. Optionally, but not necessarily, the implantable device may be sterilized within the package, e.g. by radiation or by exposure to ethylene oxide or steam. The instructions on the IFU may set forth any of the aspects of the methods of the present invention described above.

Figure 9:
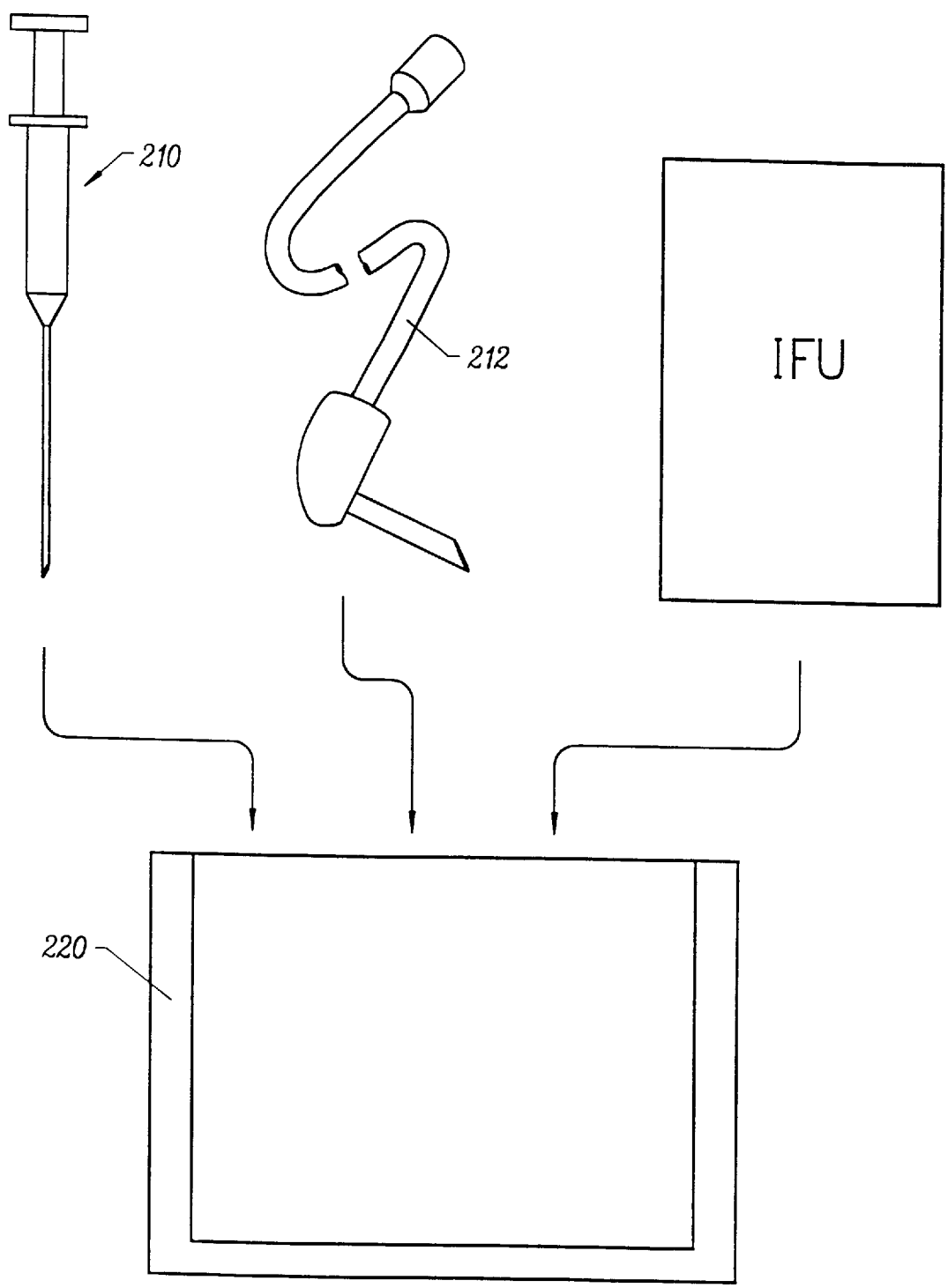
FIG. 9 illustrates a second kit according to the present invention comprising a syringe pre-loaded with a washing solution, an access tube attached to a catheter, instructions for use, and a package.

FIG. 9 illustrates a kit similar to that shown in FIG. 8, except that the kit may comprise a needle and syringe assembly 210, where the syringe is pre-loaded with a washing solution useful in the methods of the present invention. Additionally or alternatively, the kit may comprise an access tube, generally as described in the prior patent application as referenced herein above. The kit will further comprise instructions for use setting forth any of the aspects of the present invention. All or any of the components will be placed together in a common package 220, which may take any of the forms described above.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for transferring fluid between an access tube and an implanted port, said method comprising:

injecting a washing fluid into or about the implanted port through a percutaneous access tract;

introducing the access tube to the implanted port through the access tract; and transferring another fluid between the access tube and the implanted port.

2. A method as in claim 1, wherein the washing solution is selected from the group consisting of anti-microbial agents, saline, sterile water, and Ringer's solution.

3. A method as in claim 1, wherein the washing solution is injected at a volume in the range from 0.5 ml to 1000 ml.

4. A method as in claim 1, wherein the washing solution is injected from a syringe through a needle which is percutaneously introduced to the device.

5. A method as in claim 1, wherein the device is selected from the group consisting of ports, catheters, and pacemakers.

6. A method as in claim 5, wherein the device is a subcutaneously implanted port having a cannula connected to a blood vessel or other body lumen or cavity.

7. A method as in claim 1, wherein the washing solution is injected against an external surface of the device.

8. A method as in claim 7, wherein the washing solution is injected via a needle having a distal tip which is contacted against a target site on the external surface of the device, wherein the target site is not penetrated by the distal tip of the needle.

9. A method as in claim 1, wherein the washing solution is injected in to an internal volume within the device and infuses outwardly from the volume to the region surrounding the device.

10. A method as in claim 1, wherein transferring another fluid between the access tube and the implanted port comprises withdrawing blood.

11. A method as in claim 1, wherein transferring a fluid between the access tube and the implanted port comprises returning blood.

12. A method as in claim 1, wherein transferring a fluid between the access tube and the implanted port comprises infusing a drug solution.

* * * * *